United States Patent

Borzone et al.

[11] Patent Number: 5,814,070
[45] Date of Patent: Sep. 29, 1998

[54] SUTURE ANCHOR AND DRIVER

[75] Inventors: Rocco R. Borzone, Emerson; John S. Crombie, East Hanover, both of N.J.; David L. Nelson, San Francisco, Calif.

[73] Assignee: Howmedica Inc., New York, N.Y.

[21] Appl. No.: 603,478

[22] Filed: Feb. 20, 1996

[51] Int. Cl.⁶ ............................................. A61B 17/04
[52] U.S. Cl. ............................................ 606/232; 606/73
[58] Field of Search .................... 606/232, 178, 606/60, 104, 72, 73, 75

[56] References Cited

U.S. PATENT DOCUMENTS

| | | |
|---|---|---|
| 4,632,100 | 12/1986 | Somers et al. . |
| 4,716,893 | 1/1988 | Fischer et al. . |
| 4,741,330 | 5/1988 | Hayhurst . |
| 4,870,957 | 10/1989 | Goble et al. . |
| 4,898,156 | 2/1990 | Gatturna et al. . |
| 4,927,421 | 5/1990 | Goble et al. . |
| 4,968,315 | 11/1990 | Gatturna . |
| 4,988,351 | 1/1991 | Paulos et al. . |
| 5,037,422 | 8/1991 | Hayhurst et al. . |
| 5,100,417 | 3/1992 | Cerier et al. . |
| 5,152,790 | 10/1992 | Rosenberg et al. . |
| 5,156,616 | 10/1992 | Meadows et al. . |
| 5,207,679 | 5/1993 | Li . |
| 5,217,486 | 6/1993 | Rice et al. . |
| 5,224,946 | 7/1993 | Hayhurst et al. . |
| 5,234,430 | 8/1993 | Huebner . |
| 5,236,445 | 8/1993 | Hayhurst et al. . |
| 5,258,016 | 11/1993 | DiPoto et al. ............................ 606/232 |
| 5,324,308 | 6/1994 | Pierce . |
| 5,364,400 | 11/1994 | Rego, Jr. et al. . |
| 5,370,662 | 12/1994 | Stone et al. . |
| 5,372,599 | 12/1994 | Martins . |
| 5,383,905 | 1/1995 | Golds et al. . |
| 5,443,482 | 8/1995 | Stone et al. . |
| 5,522,844 | 6/1996 | Johnson ................................... 606/232 |
| 5,534,011 | 7/1996 | Greene, Jr. et al. ..................... 606/232 |
| 5,573,548 | 11/1996 | Nazre et al. ............................. 606/232 |
| 5,584,835 | 12/1996 | Greenfield ................................ 606/73 |
| 5,584,860 | 12/1996 | Goble et al. ............................. 606/232 |

FOREIGN PATENT DOCUMENTS

| | | |
|---|---|---|
| 0 465 910 A | 1/1992 | European Pat. Off. . |
| WO 88 09157 A | 12/1988 | WIPO . |

OTHER PUBLICATIONS

Daniel, Dale M. and DePuy, product literature entitled "Soft Tissue Fixation Washers".

Mitek surgical product brochure entitled "High Strength – Mitek GII Anchor" (1991).

Zimmer product brochure entitled "Statak™ Soft Tissue Attachment Device".

Acufex product brochure entitled "TAG™ Tissue Anchor Guide System".

Zimmer product brochure entitled "Mini–Statak™ Soft Tissue Attachment Device" (1992).

*Primary Examiner*—Michael Powell Buiz
*Assistant Examiner*—Tina T. D. Pham
*Attorney, Agent, or Firm*—Pennie & Edmonds LLP

[57] ABSTRACT

A suture anchor and driver device is described that is designed to secure a suture anchor to a bone in a patient to allow soft tissue or the like to be secured to the bone. The suture anchor itself engages the suture along the length of a passage that passes through the diameter of the distal end of the suture anchor, providing for a relatively large area of engagement to minimize stress on the suture material. The driver is designed to engage the suture anchor and guide the suture material along outside surface of the driver.

24 Claims, 6 Drawing Sheets

SUTURE ANCHOR AND DRIVER

BACKGROUND

The present invention generally relates to suture anchors and drivers. Specifically, the present invention relates to a suture anchor and driver device that allows for the improved implantation of suture anchors in an efficient, simple manner.

There are several existing devices that can be used to secure soft tissue to bone. Devices such as screws and staples have been known in the art for several years, but are difficult to insert, and can cause damage to the bone tissue when they are inserted. In addition, if the devices must be later removed, they can cause further damage to the bone and surrounding tissue. More recently, suture anchors have been designed that are specifically adapted to secure a suture to attach soft tissue such as ligaments, to bone.

For example, in U.S. Pat. No. 5,370,662 to Stone et al., a suture anchor assembly is described in which the suture anchor has a threaded portion with a self-tapping screw at one end for attachment to the bone, and an eyelet at the other end for receiving a suture. The suture anchor is also designed to be coupled to a rotating driver device. The suture anchor and driver fit together in an interlocking fashion. The disadvantage of the Stone patent is the way in which the suture itself is threaded through an eyelet and then threaded inside the driver. The actual threading of the suture inside the driver is a difficult additional step for a surgeon or nurse to perform, and must be performed for every suture anchor to be implanted. This design also creates a single point of stress on the suture material at the eyelet of the suture anchor, which increases the chance of breakage. In addition, because the suture material is within the driver, the status of the suture material cannot be monitored by a surgeon during the surgical procedure.

Thus, the prior art has failed to provide a suture anchor that can provide a secure fixation to a bone that allows for simple and efficient implantation.

SUMMARY OF INVENTION

The object of the present invention is to provide a suture anchor and driver with a novel design that allows a surgeon to easily implant a suture anchor using a novel interlocking driver to create a secure base for a suture.

Specifically, it is an object of the present invention to provide a suture anchor and driver device that allows a surgeon to view the suture material during the implantation process.

It is a further object of the invention to provide a suture anchor and driver device that is capable of securing more than one strand of suture material.

It is a further object of the invention to provide a suture anchor and driver device that is capable of being "preloaded" with suture material, to allow a surgeon to implant a number of suture anchors during a single operative procedure.

It is a further object of the present invention to provide a suture anchor which engages a length of suture material at the distal end over a distributed area to minimize the chance of suture breakage.

It is a further object of the present invention to provide a suture anchor that does not require suture material to be threaded through a small opening.

These and other objects are achieved with a suture anchor and driver device that includes a suture anchor with a proximal end for insertion into bone tissue, a central threaded portion, and a distal end of substantially cylindrical shape having a diameter through a central axis. The distal end defines a passage that passes through the diameter, and is preferably large enough to allow at least two strands of suture material to pass through freely. The driver is releasably engaged with the distal end of the suture anchor.

The suture anchor and driver define a suture path along the outside surface of the driver in a longitudinal fashion, through the passage defined by the distal end of said suture anchor, and returning along the outside surface of the driver in a longitudinal fashion.

The distal end of the suture anchor also helps define the suture path through the provision of two grooves located at the ends of the passage, which aid in guiding the suture material from the passage in a longitudinal distal direction. The distal end is further provided with a U-shaped groove to mate with the proximal end of the driver, which has a U-shaped protrusion.

The driver also includes a flange adapted to aid the user in positioning said suture anchor and driver device by preventing the driver from being inserted too far. A tissue protector tube is also provided to fit over the anchor and driver device to help with the initial insertion of the device through soft tissue and to engage the bone surface. The driver also includes a suture retainer to hold the ends of the suture material in place, and a handle which may be coupled to the distal end.

DETAILED DESCRIPTION

Figure 1:
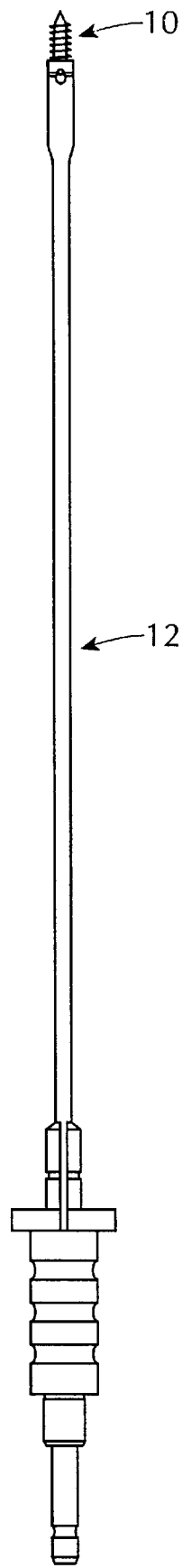
FIG. 1 is a side plan view of the preferred embodiment of the suture anchor and driver device.

The preferred embodiment of suture anchor 10 and driver 12 are illustrated in FIG. 1, coupled together for use in anchoring a suture to a bone.

The suture anchor 10, shown in FIGS. 2–5 has a proximal region 14 which is inserted into the desired bone, and a distal region 16 which is adapted to secure a suture or other desired thread-like material and to engage the driver 12. At the farthest proximal end of the proximal region, the suture anchor 10 is provided with a cutting tip 18 to facilitate the insertion into the bone. Cutting tips are generally known, and the cutting tip 18 used for the present invention may be of any design known in the art.

The proximal region 14 of the suture anchor 10 further camprises a threaded portion, so that once the tip 18 is engaged with the surface of the bone, rotation of the suture anchor 10 will cause the anchor 10 to enter the bone tissue. The threaded portion can be constructed in any manner known in the art of suture anchors.

Figure 2:
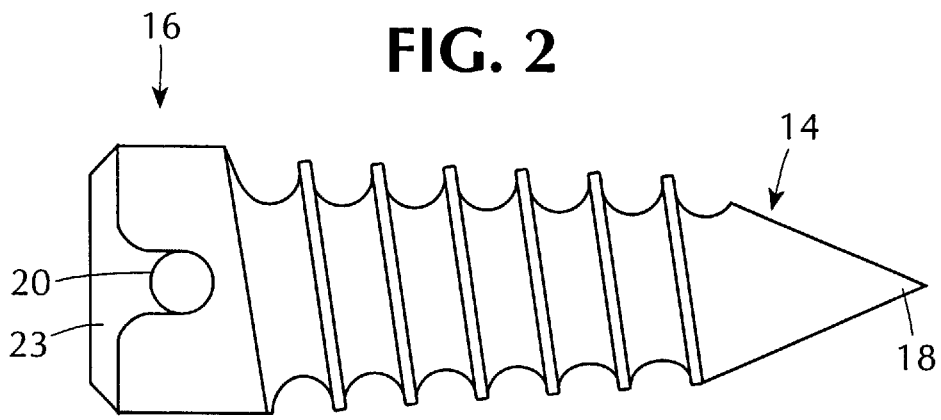
FIG. 2 is a side plan view of the suture anchor.
Figure 4:
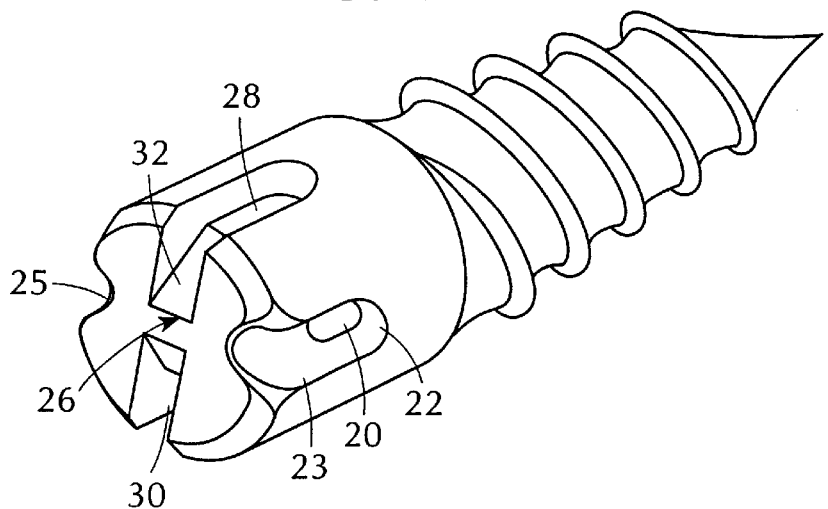
FIG. 4 is a perspective view of the distal end of the suture anchor.

The distal region 16 has a novel design intended to facilitate both the securing of the suture material to the anchor and the engagement of the suture anchor with the driver. The securing of the suture material is achieved through the provision of a cradle 20 which defines a U-shaped passage through the diameter of the distal region 16. The cradle 20, as shown in FIGS. 2 and 4, preferably defines a passage that has a diameter sufficiently large to allow at least one strand of suture material to pass through freely, and preferably large enough to allow two strands of suture material to pass through the distal region 16 freely. By allowing two strands of suture material to be secured by the suture anchor, the surgeon may use the device for attachments that have a particular need for an extremely strong connection between the suture anchor and the soft tissue. The cradle 20 also provides an advantage in that the area of stress of the suture material is maximized along the curved length of the cradle 20. This design minimizes the risk of breakage of the suture material, which would be increased in conventional eyelet designs. The two exit holes of the cradle, 22 and 24, are located on opposing sides of the distal region of the anchor.

Figure 2A:
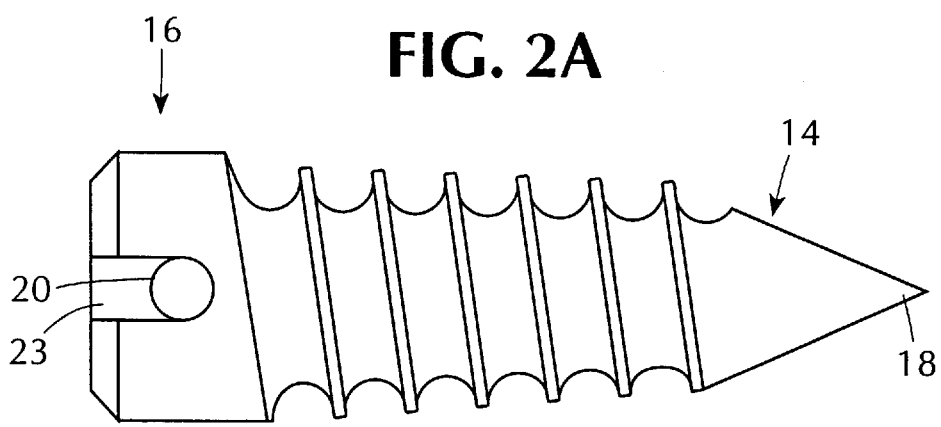
FIG. 2A is a side plan view a first alternative embodiment of the suture anchor.
Figure 3:
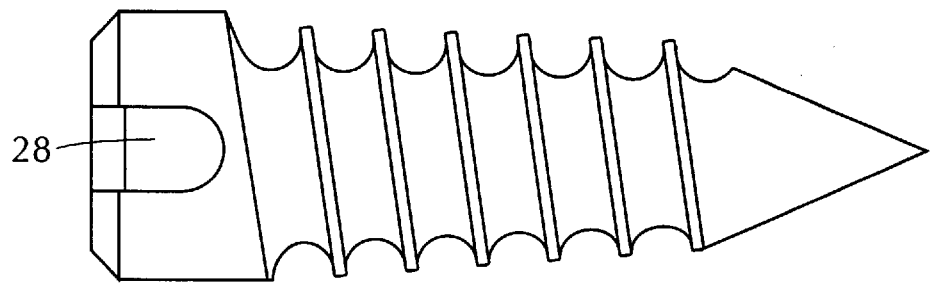
FIG. 3 is a side plan view of the suture anchor, rotated 90 degrees from FIG. 2.
Figure 5:
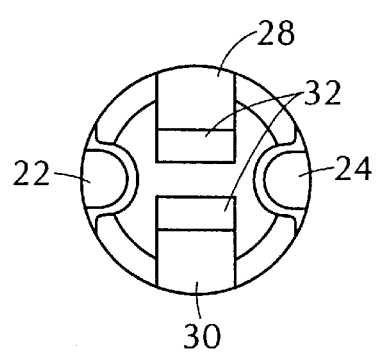
FIG. 5 is an end view of the distal end of the suture anchor.
Figure 5A:
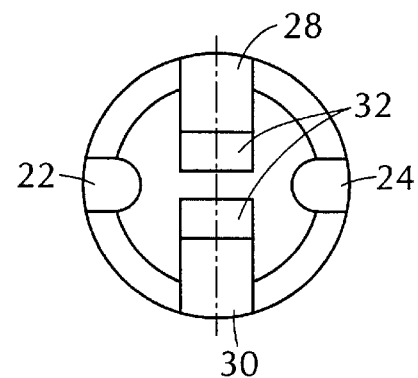
FIG. 5A is an end view of the distal end of the first alternative embodiment of the suture anchor.

The novel suture anchor design allows for the suture material to be located at the outside diameter of the distal region 16 of the anchor 10 (where the exit holes 22 and 24 are located). From the outside diameter, the suture material is guided out the exit holes 22 and 24, and along grooves 23, 25, which are located at each exit hole and extend longitudinally in the distal direction (towards the driver). The area where the grooves 23, 25 meet the distal end of the suture is preferably curved, as shown in FIGS. 2 and 5, to allow some lateral movement of the suture without the risk of catching the suture on a corner. If easier construction is desired, however, the first alternative embodiment, showm in FIGS. 2A and 5A, illustrate the form of the distal end of the alternative suture in which the corners where the grooves 23, 25 meet the distal end are not curved. The path of the suture then extends along the outside surface of the driver 12, which is described in more detail below.

The distal region 16 of the suture anchor is also designed to facilitate interconnection with the driver 12. For this purpose, the distal region 16 has a U-shaped groove 26, illustrated in FIGS. 3–5, that mates with a U-shaped protrusion on the proximal end of the driver 12, which will be discussed below. The U-shaped groove has three components. There is a first side groove 28, which extends longitudinally in the distal region 16. A second side groove 30 extends longitudinally in the opposite side of the distal region 16. Connecting these two grooves is a central end groove 32, which runs along a diameter of the suture anchor.

Figure 6:
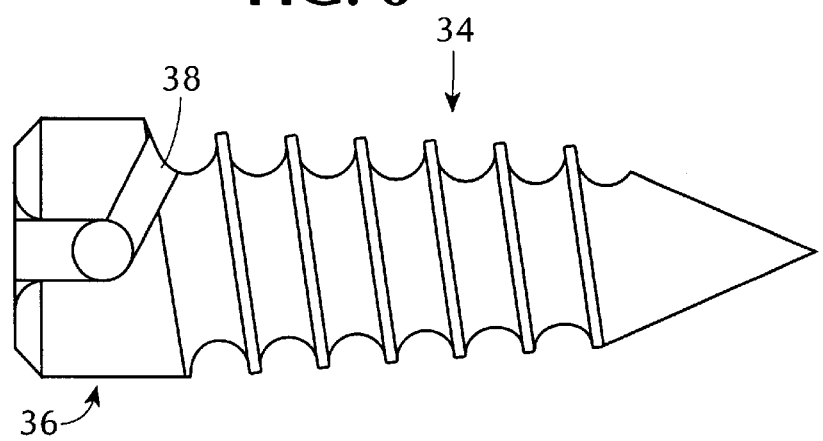
FIG. 6 is a side plan view of the second alternative embodiment of the suture anchor.

An second alternative embodiment 34 of the suture anchor is shown in FIG. 6. The alternative suture anchor 34 has a novel distal end 36 designed to engage the suture material without the need to thread the suture material through a small opening. The anchor 34 is provided with slot 38 which defines the passage for the suture material. The slot is preferably constructed so that the suture material will remain in the slot if the ends of the suture material are held in the distal direction. Therefore, the slot is should be designed to form at least a ninety degree angle with the central axis of the suture anchor, and preferably forms an angle of greater than ninety degrees with the central axis of the distal end of the suture anchor. The alternative anchor 34 provides the same advantage of distributing the stress on the suture material over the diameter of the distal end, with the added advantage of elimination of the need to "thread" the suture material. A length of suture material is simply placed in the slot 38, and will remain securely attached to the anchor 34 as long as the two ends of the suture material are under tension in the distal direction. Therefore, when using the alternative anchor 34, care must be taken that tension is maintained while the anchor 34 is implanted. As will be further discussed below, the driver 12 is designed to maintain the suture material under tension during the implantation process.

The suture anchor 10 or alternative anchor 34 are preferably manufactured of a lightweight, biocompatible material, most preferably titanium. Alternatively, the suture anchor 10 or 34 can be manufactured of a bioabsorbable material, or partially absorbable material of sufficient strength.

Figure 7:
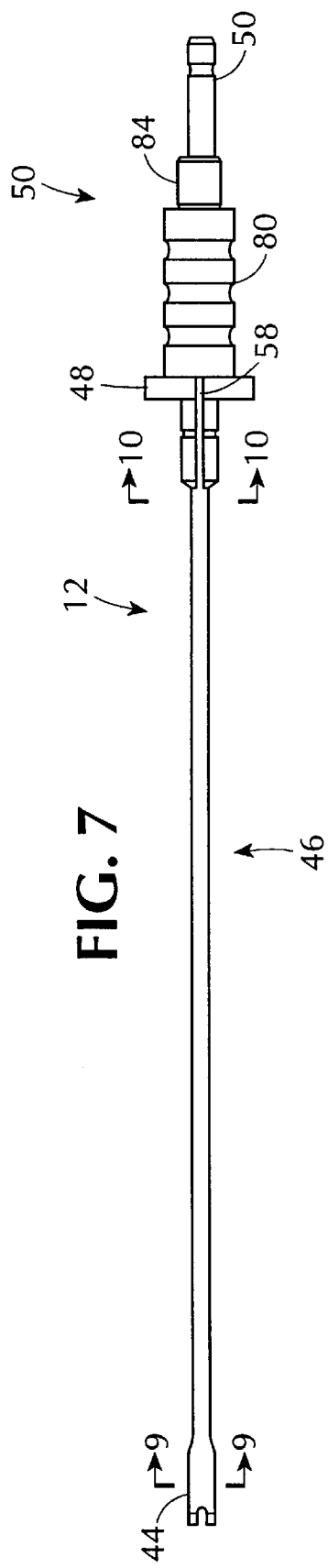
FIG. 7 is a side plan view of the driver.

As seen in FIG. 7, the driver 12 has a proximal region 44 for engaging the suture anchor 10, an elongated central portion 46, a flange 48, and a distal region 50, adapted to secure the excess suture material and engage the driver to a handle 52.

Figure 8:
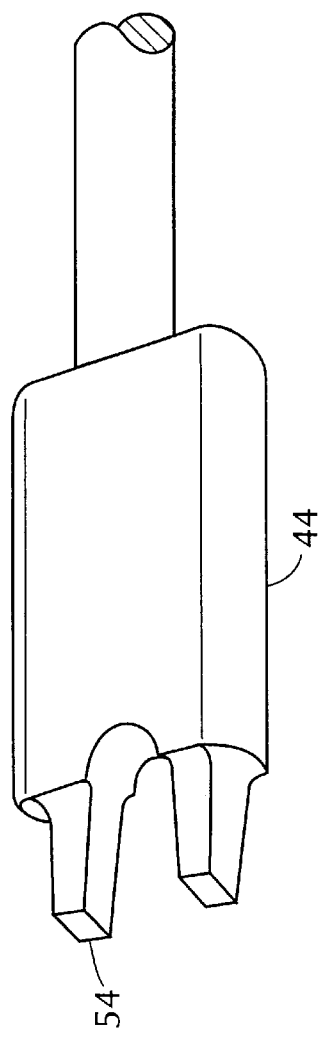
FIG. 8 is a perspective view of the proximal end of the driver shown in FIG. 7.

The proximal region 44 of the driver 12, shown in FIG. 8, mates with the distal region 14 of the suture anchor 10. As described above, the distal region 14 of the suture anchor 10 has a U-shaped groove 26. The proximal region 44 of the driver 12 accordingly has a U-shaped protrusion 54 at the most proximal end, which mates with the distal end of the anchor. The interlocking arrangement allows the rotation of the driver to rotate the suture anchor 10 into the bone. The arrangement also allows the driver to be quickly and easily released from the suture anchor once the anchor 10 is implanted in the bone.

Figure 9:
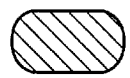
FIG. 9 is a cross-sectional view through line A–A' of FIG. 7.

The proximal region 44 has a generally rectangular cross-section, as shown in FIG. 9. The widest portion of the proximal region corresponds with the diameter of the distal end 16 of the suture anchor. Therefore, the circular profile of the suture anchor defines the maximum size of the passage created in tissue to use the anchor and driver device, which will minimize the trauma to surrounding tissue. This design also allows a user of the device to countersink the hole created by the anchor and driver device, which was not possible in prior art devices in which the driver mechanism has a larger cross-sectional area. The present invention also allows a user to remove suture anchors after bone tissue has grown around the anchor, and only a small driver could access the tip of the anchor.

The elongated central portion 46 extends longitudinally from the proximal region 44 that engages the suture anchor. The elongated central portion has a generally circular cross-section, which is of a smaller diameter than the suture anchor, to ensure that the addition of suture material along the central portion will not create a cross-sectional profile larger than that of the suture anchor itself.

Figure 10:
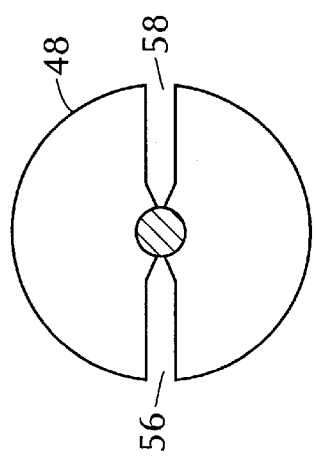
FIG. 10 is a cross-sectional view through line B–B' of FIG. 7.

The flange 48 extends radially from the central axis of the driver. The flange 48 is further provided with two grooves 56, 58, shown in FIG. 10 that terminate slightly past the location of the flange 48. The grooves 56, 58 guide the suture material along the driver without interruption by the flange 48. In use, the suture material will extend from exit holes of the cradle 20 of the suture anchor, along the grooves provided on the suture anchor, further along the flattened proximal portion of the driver 44, along the elongated central portion 46, and along the grooves 56, 58 formed by the flange 48. The suture material may also be wrapped around the central portion 46 if excess suture material is desired. The flange 48 also prevents the driver from being inserted too far into a patient when used in conjunction with the tissue protection tube 70, which will be described below.

Figure 11:
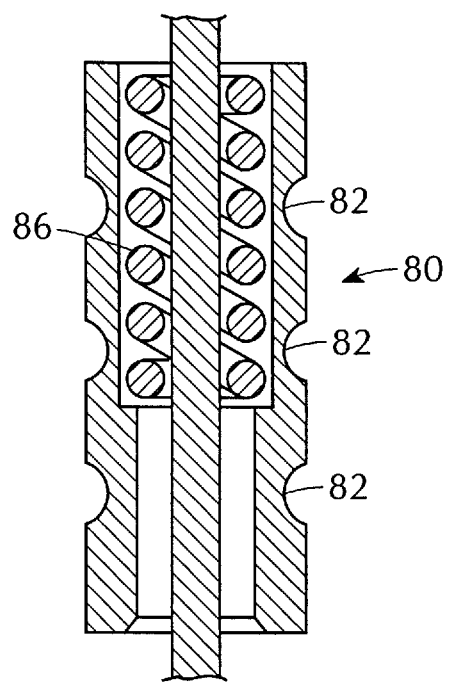
FIG. 11 is a cross-sectional view of the suture retainer through the central axis of the driver.

The driver 12 is further provided with a suture retainer 80, which holds the ends of the suture material tautly during the implantation procedure. The suture retainer 80 has a spring-release arrangement with the driver 12, as shown in FIG. 7. The spring-release arrangement holds the suture material in place against the flange 48 when the retainer 80 is in the relaxed position. When the retainer 80 is moved in the distal direction, an opening is created between the retainer 80 and the flange 48, allowing the suture material to be released. The retainer 80 is preferably provided with grooves 82 to make movement of the retainer easier. The suture retainer 80 is shown in cross-section along the central axis of the driver in FIG. 11. FIG. 11 illustrates the spring 86 which maintains the suture retainer 80 in a relaxed position against the distal surface of the flange 48, and is compressed by the movement of the retainer against stop 84.

Alternative ways of securing the loose ends of the suture material could also be utilized in conjunction with the suture anchor and driver device of the present invention. For example, a suture retainer could also be designed to engage the driver with screw means, so that rotating the retainer would loosen the screw means to allow the suture material to be released. Other designs in which the suture material could be held tautly and then released when necessary could also be used.

Figure 12:
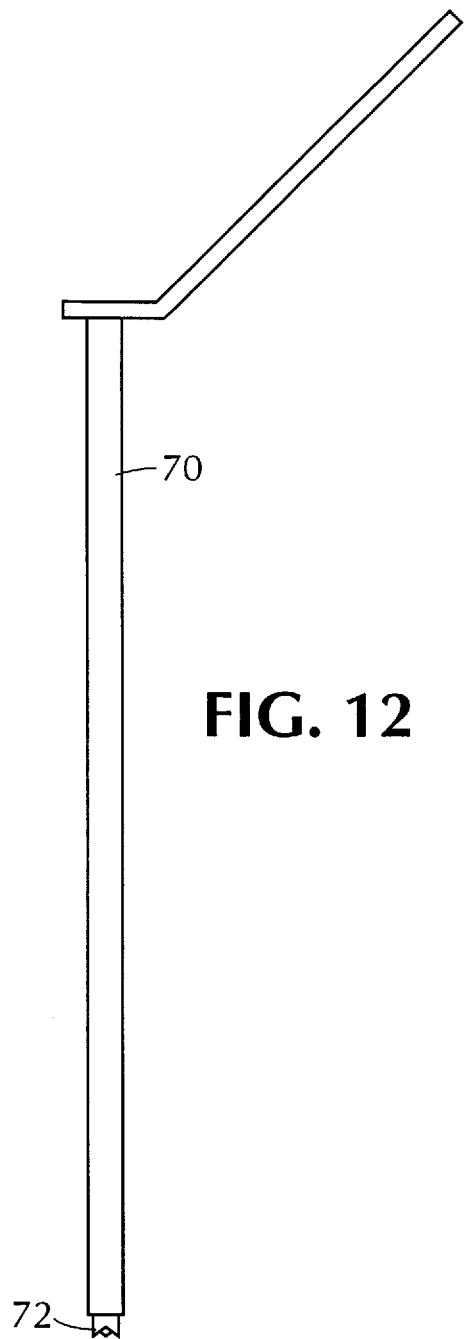
FIG. 12 is a side plan view of the tissue protector.
Figure 13:
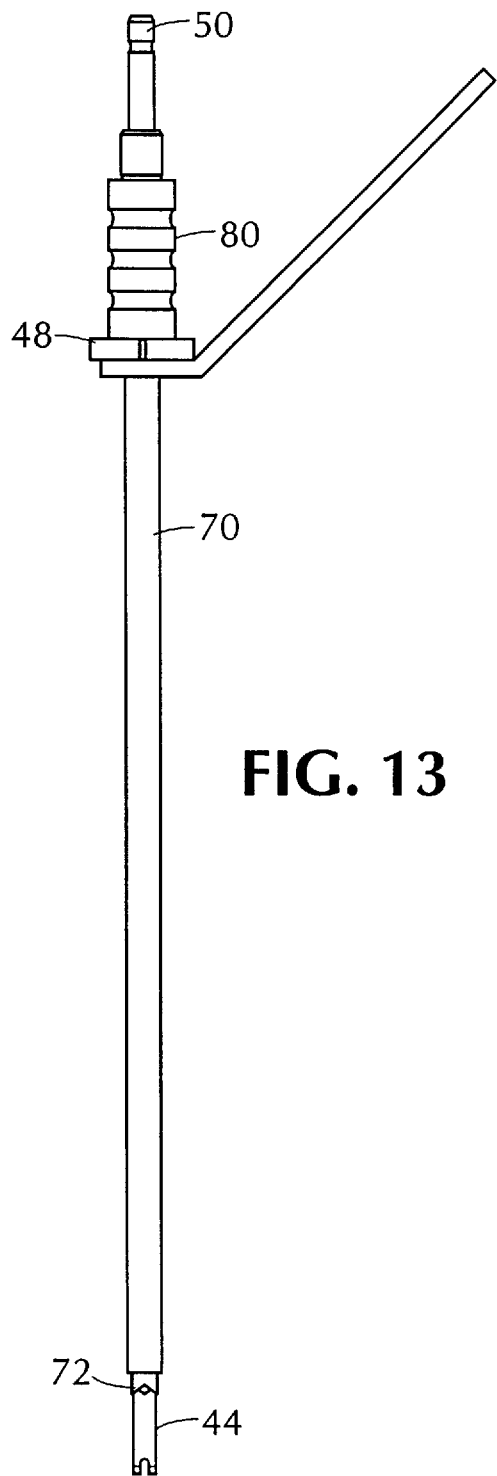
FIG. 13 is a side plan view of the tissue protector on the driver.

The suture anchor and driver device is preferably provided with a tissue protector tube 70. The tube 70, as shown in FIG. 12, is placed over the driver 12 after the suture material has been threaded through the suture anchor 10 and secured by the suture retainer of the driver. The tube 70, which is preferably made of stainless steel, is simply slipped over first the suture anchor 10 and then the driver 12, up to the flange 48, which acts as a "stop" to prevent the tube 70 from moving too far up the driver. The function of the tube 70 is to provide a smooth barrier between the driver 12 and suture material along the sides of said driver and the tissue of the patient. The tube 70 prevents the suture material or the anchor itself from being caught or snagged, and allows smooth entry through the tissue of the patient. The tube 70 also helps in the initial engagement of the bone surface, through the provision of teeth 72 on the proximal end of the tube 70. In use, the tube 70 may be first inserted into the patient to engage the bone tissue in the desired location, and then the suture and driver device can be inserted from the back of the tube 70. The tube 70 is shown over the driver device in FIG. 13. The strong initial placement allows the surgeon to position the anchor and driver device in the desired location.

Figure 14:
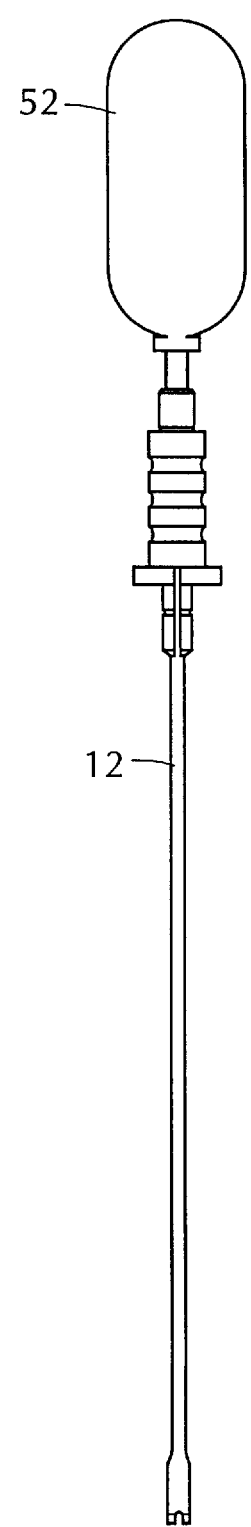
FIG. 14 is a side plan view of the driver coupled with a handle.

The distal end 50 of the driver 12 is designed to releasably engage a handle 52. The distal end 50 shown in FIG. 7 is specifically designed to engage a standard handle 52 available from HOWMEDICA, as shown in FIG. 14. The distal end 50 could, however, be designed to engage any particular type of handle. The quick release coupling design shown in FIG. 7 provides the surgeon with a particular advantage for procedures in which more than one suture anchor is to be implanted. Several suture anchor and driver devices can be pre-loaded with suture material before an operation begins. Once the incision is made, the first suture anchor is implanted using the driver and handle, and then the handle can be released from the driver, and engaged with a second pre-loaded anchor and driver device for an additional implant. In addition, the distal end 50 can be attached to a power source, such as a power drill to aid in inserting the anchor.

We claim:

1. A suture anchor and driver device comprising:

a suture anchor, said anchor comprising a proximal end for insertion into bone tissue, a central threaded portion, and a distal end of generally cylindrical shape having a diameter through a central axis, wherein said distal end is adapted to define a passage along the diameter of said distal end, and is further adapted to engage a driver;

a driver having a proximal end releasably engaged with the distal end of said suture anchor, and an elongated central portion with a substantially cylindrical outer surface;

wherein said suture anchor and driver are adapted to define a suture path along the outside surface of said driver in a longitudinal fashion, along the passage defined by the distal end of said suture anchor, and returning along the outside surface of said driver in a longitudinal fashion; and wherein the distal end of the suture anchor has a first cross-sectional area and the central portion of the driver has a third cross-sectional area, and wherein said first cross-sectional area is greater than said third cross-sectional area.

2. The suture anchor and driver device of claim 1 wherein the passage defined by the distal end of said suture anchor further defines two ends of said passage, each said end being located on opposing sides of said distal end, wherein the distal end is further adapted to define two grooves located opposing sides of said distal end, wherein a first said groove begins near the first end of said passage and the second said groove begins near the second end of said passage, and said first and second grooves extend longitudinally in the distal direction.

3. The suture anchor and driver device of claim 1 wherein said distal end further defines a U-shaped groove which extends longitudinally along opposing sides of said distal end and across a diameter of said distal end.

4. The suture anchor and driver device of claim 3 wherein the proximal end of said driver designed to engage the distal end of said suture anchor, wherein said proximal end further comprises a U-shaped protrusion.

5. The suture anchor and driver device of claim 1 wherein said driver further comprises a flange located at the distal end of said elongated central portion, adapted to aid the user in positioning said suture anchor and driver device.

6. The suture anchor and driver device of claim 5 wherein said device further includes a tissue protector tube adapted to fit over said driver.

7. The suture anchor and driver device of claim 1 wherein said driver further comprises a suture retainer adapted to hold suture material in place.

8. The suture anchor and driver device of claim 1 wherein said driver is releasably coupled to a handle.

9. The suture anchor and driver device of claim 1 wherein said passage is defined by said distal end of the suture anchor to allow at least two strands of suture material to pass through said passage.

10. The suture anchor and driver device of claim 1 wherein the proximal end of the driver has a second cross-sectional area, and wherein the first cross-sectional area of the distal end of the suture anchor is greater than said second cross-sectional area.

11. A suture anchor and driver device comprising:
   a suture anchor, said anchor comprising a proximal end for insertion into bone tissue, a central threaded portion, and a distal end of substantially cylindrical shape having a diameter through a central axis and an outer circumference, wherein said distal end is adapted to define a passage and a slot, wherein the passage is along the diameter of said distal end and the slot extending outwardly from said passage to the circumference of the suture anchor, and wherein said distal end is further adapted to engage a driver;
   a driver having a proximal end releasably engaged with the distal end of said suture anchor, and an elongated central portion with a substantially cylindrical outer surface; and
   wherein said suture anchor and driver are adapted to define a suture path along the outside surface of said driver in a longitudinal fashion, through the passage defined by the distal end of said suture anchor, and returning along the outside surface of said driver in a longitudinal fashion.

12. The suture anchor and driver device of claim 11 wherein the diameter of said distal end along said slot has a first end and second end, and wherein said distal end is adapted to define first and second grooves located on opposing sides of said distal end, wherein said first groove begins near the first end of said diameter and said second groove begins near the second end of said diameter, and said first and second grooves extend longitudinally in the distal direction.

13. The suture anchor and driver device of claim 11 wherein said distal end is further adapted to define a U-shaped groove.

14. The suture anchor and driver device of claim 13 wherein the proximal end of said driver designed to engage the distal end of said suture anchor, wherein said proximal end further comprises a U-shaped protrusion.

15. The suture anchor and driver device of claim 11 wherein the distal end of the suture anchor has a first cross-sectional area and the proximal end of the driver has a second cross-sectional area, and wherein the first cross-sectional area is greater than said second cross-sectional area.

16. The suture anchor and driver device of claim 15 wherein the central portion of said driver has a third cross-sectional area, wherein said first cross-sectional area is greater than said third cross-sectional area.

17. The suture anchor and driver of claim 11 wherein said driver further comprises a flange located at the distal end of said elongated central portion adapted to aid the user in positioning said suture anchor and driver device.

18. The suture anchor and driver device of claim 11 wherein said device further includes a tissue protector tube adapted to fit over said driver.

19. The suture anchor and driver device of claim 11 wherein said driver further comprises a suture retainer adapted to hold suture material in place.

20. The suture anchor and driver device of claim 11 wherein said driver is releasably coupled to a handle.

21. The suture anchor and driver device of claim 11 wherein said passage is defined by said distal end of the suture anchor to allow at least two strands of suture material to pass through said passage.

22. The suture anchor and driver device of claim 11 wherein the slot is at an angle of at least ninety degrees with the distal end of the central axis.

23. A suture anchoring device comprising:
   a suture anchor, said anchor comprising a proximal end for insertion into bone tissue, a central threaded portion, and a distal end of substantially cylindrical shape having a diameter through a central axis, wherein said distal end is adapted to define a passage along the diameter of said distal end, wherein the passage defined by the distal end of said suture anchor further defines first and second ends of said passage, said ends located on opposing sides of said distal end, wherein the distal end is adapted to define first and second grooves located on opposing sides of said distal end, wherein said first groove begins near the first end of said passage and said second groove begins near the second end of said passage, and said first and second grooves extend longitudinally in the distal direction, and wherein said distal end further defines a U-shaped groove adapted to engage a driver;
   a driver releasably engaged with the distal end of said suture anchor, said driver having a substantially cylindrical outer surface, and wherein said driver comprises:
      a proximal end designed to engage the distal end of said suture anchor, wherein said proximal end further comprises a U-shaped protrusion;
      a flange adapted to aid the user in positioning said suture anchor and driver device; and
   wherein said suture anchor and driver are adapted to define a suture path along the outside surface of said driver in a longitudinal fashion, through the passage defined by the distal end of said suture anchor, and returning along the outside surface of said driver in a longitudinal fashion; and
   wherein the distal end of the suture anchor has a first cross-sectional area and the central portion of the driver has a third cross-sectional area, and wherein said first cross-sectional area is greater than said third cross-sectional area.

24. A suture anchoring device comprising:
   a suture anchor, said anchor comprising a proximal end for insertion into bone tissue, a central threaded portion, and a distal end of substantially cylindrical shape having a diameter through a central axis and an outer circumference, wherein said distal end is adapted to define a passage and a slot, wherein the passage is along the diameter of said distal end and the slot extending outwardly from said passage to the circumference of the suture anchor, wherein the passage defined by the distal end of the suture anchor has a first and second end, and wherein said distal end is adapted to define first and second grooves located on opposing sides of said distal end, wherein said first groove begins near the first end of said passage and said second groove begins near the second end of said passage, and said first and second grooves extend longitudinally in the distal direction, and wherein said distal end is further adapted to define a U-shaped groove to engage a driver;

a driver having a proximal end releasably engaged with the distal end of said suture anchor, and an elongated central portion with a substantially cylindrical outer surface, and wherein said driver comprises:
   a proximal end designed to engage the distal end of said suture anchor, wherein said proximal end further comprises a U-shaped protrusion;

a flange adapted to aid the user in positioning said suture anchor and driver device; and wherein said suture anchor and driver are adapted to define a suture path along the outside surface of said driver in a longitudinal fashion, through the passage defined by the distal end of said suture anchor, and returning along the outside surface of said driver in a longitudinal fashion.

\* \* \* \* \*